United States Patent [19]

Biehl et al.

[11] Patent Number: 4,979,376
[45] Date of Patent: Dec. 25, 1990

[54] MICROTOMY DEVICE

[76] Inventors: Manfred Biehl, Eschelbronner Strasse 35, D-6922 Meckesheim; Gernot Hansel, Gerstenstrasse 31, D-7000 Stuttgart 70; Hans Heid, Schubertstrasse 24, D-6901 Bammental; Manfred Kempe, Untere Eulenscheide 17, D-6903 Neckargemund; Dieter Teppke, Buchenweg 16, D-6830 Schwetzingen; Jurgen Vierling, Friedenstrasse 4, D-6904 Eppelheim, all of Fed. Rep. of Germany

[21] Appl. No.: 418,402

[22] Filed: Oct. 6, 1989

[30] Foreign Application Priority Data

Oct. 10, 1988 [DE] Fed. Rep. of Germany ... 8812708[U]

[51] Int. Cl.$^5$ ............................................. F25D 23/00
[52] U.S. Cl. ......................................... 62/264; 62/320; 49/171; 220/254; 83/915.5
[58] Field of Search ............... 62/320, 248, 264; 83/915.5; 312/292; 49/169–171; 220/254–256

[56] References Cited

U.S. PATENT DOCUMENTS

| | | | |
|---|---|---|---|
| 3,204,424 | 9/1965 | McCormick et al. | 62/320 |
| 3,218,896 | 11/1965 | McCormick | 83/915.5 X |
| 3,233,965 | 2/1966 | McCormick | 83/915.5 X |
| 3,236,133 | 2/1966 | De Pas | 83/915.5 X |
| 3,405,281 | 10/1968 | Wilson | 62/264 X |
| 3,414,713 | 12/1968 | Reifeiss et al. | 62/248 X |
| 4,548,051 | 10/1985 | Moessner | 62/320 |

OTHER PUBLICATIONS

Reichert–Jung, 975C Cryostat.
Reichert–Jung, 2800 Frigocut.

*Primary Examiner*—William E. Tapolcai
*Attorney, Agent, or Firm*—Bean, Kauffman & Spencer

[57] ABSTRACT

An improve microtomy device is disclosed comprising a microtome and a thermostatically controlled refrigeration means controllable by a microprocessor and accommodated in an instrument cabinet, the improvement comprising, providing an upper part of the instrument cabinet in the form of a movable cover, which cover encloses a slidable transparent pane arranged above the microtome to define an inspection window disposed in a front portion of the cover. The pane is heatable and can be removed from the cover and/or shifted into a rearward portion of the cover to open the inspection window for cleaning purposes. The improved device provides convenient accessibility to the interior of the instrument and improved control of operations.

15 Claims, 3 Drawing Sheets

U.S. Patent   Dec. 25, 1990   Sheet 3 of 3   4,979,376
Fig. 4.
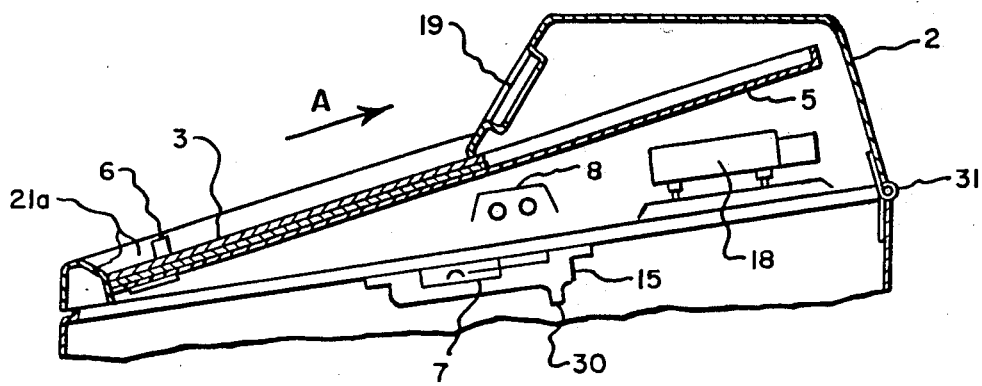
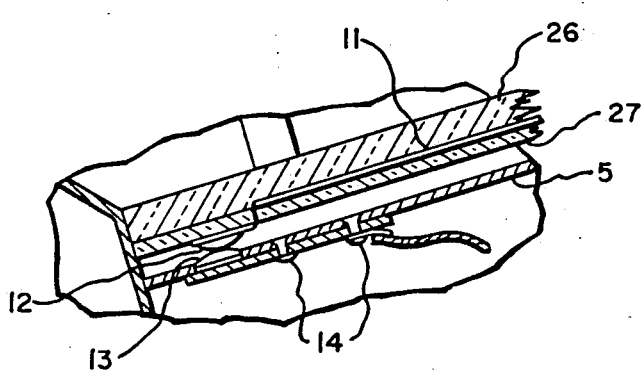
Fig. 5.
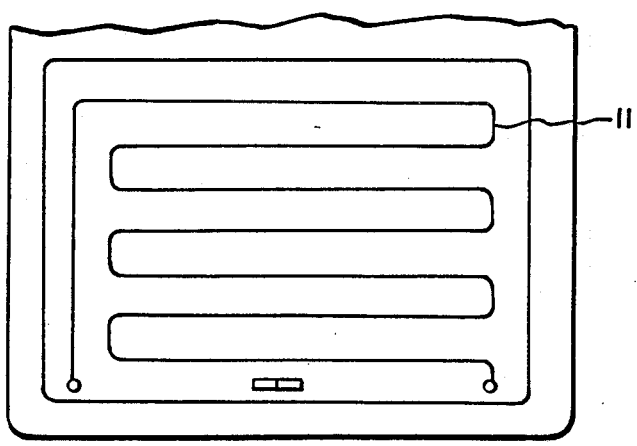
Fig. 6.

MICROTOMY DEVICE

The invention relates to a microtomy device wherein a microtome and a thermostatically controlled refrigeration means are accommodated in an instrument cabinet, according to the preamble of claim 1.

SUMMARY OF THE INVENTION

The invention is based on the object of improving a device of the above-mentioned type such that it is of small dimensions, can be easily transported and the interior is readily accessible. Moreover, all functions of the device are easily controllable by the operator of the device.

According to the invention, this object is solved by the features indicated in the characterizing part of claim 1, particularly that the upper part of the instrument cabinet is in the form of a frame(cover) which can be folded (pivoted) away from the instrument cabinet, which frame encloses a shiftable transparent, preferably glass, pane arranged above the microtome which defines an inspection window disposed in the front portion of the foldaway frame, which glass pane can be shifted into the rearward portion of the frame to provide a means to open said inspection window and which glass pane can be removed from the frame for cleaning purposes.

Further details of the invention are evident from the subclaims and the description. In subclaim 2, the pane is provided with a heating means connectable to a power supply provided in the device by means of contacts which automatically engage when the shiftable pane is in its advanced and closed position. A glass pane is provided with asymmetric heating wires such that the heating power at the front window portion is higher than at the rearward window portion in subclaim 3. In subclaim 4, the microtome is accommodated in a vessel preferably made of special(stainless) steel, said vessel being arranged under the inspection window and, for cleaning purposes, provided with a discharge. In subclaim 5, a mechanical means for driving the microtome is provided on the sidewall of the desk-shaped instrument cabinet. In subclaim 6, the microtome is provided with a rapid-exchange means for changing the preparation in the installed condition of the microtome within the instrument cabinet. In subclaim 7, a daylight (fluorescent) object illuminator is arranged above the cutting edge of the microtome. In subclaim 8, the instrument cabinet is of self contained construction without a frame, and a substantially trough-shaped aggregate (assembly) support is suspended in the lower part of the cabinet to reinforce the same. In subclaim 9, the refrigeration aggregate(assembly) as well as the electric aggregates(assemblies) for the device are mounted in the suspended aggregate(assembly) support. In subclaim 10, plastic-coated slide rails are provided on the back of a desk-shaped instrument cabinet to allow the device to be horizontally placed and moved in smaller transport vehicles. In subclaim 11, guide rollers are provided on the underside of a desk-shaped instrument cabinet, which rollers can be rotated by 360° and are arrestable, at least in part, by means of stoppers. In subclaims 12 and 13, a microprocessor comprising two control boards is provided for controlling all aggregates of the device including the microtome functions, one of said control boards being associated with the processor and the second one with the keyboard which comprises a liquid crystal display means and function keys. In subclaim 14, the display means is an alphanumeric display means. In subclaim 15, the display means in the foldaway frame is disposed above the inspection window and arranged at an angle from the horizontal which is more obtuse than that enclosed between the horizontal and the inspection window. In subclaim 16, the liquid crystal display comprises a menu line from which functions can be selected by means of the function keys and a status line.

One embodiment of the invention will now be described by way of example with reference to the accompanying drawings.

DESCRIPTION OF THE DRAWINGS

FIG. 4 is a sectional view of the foldaway frame (cover) taken approximately along line 4—4 of FIG. 1.

FIG. 5 is an enlarged sectional view of the connecting contacts of the heatable pane taken approximately along line 5—5 of FIG. 1.

FIG. 6 is a plan view of the heatable pane, including the arrangement of the heating wires.

DETAILED DESCRIPTION OF THE INVENTION

Figure 1:
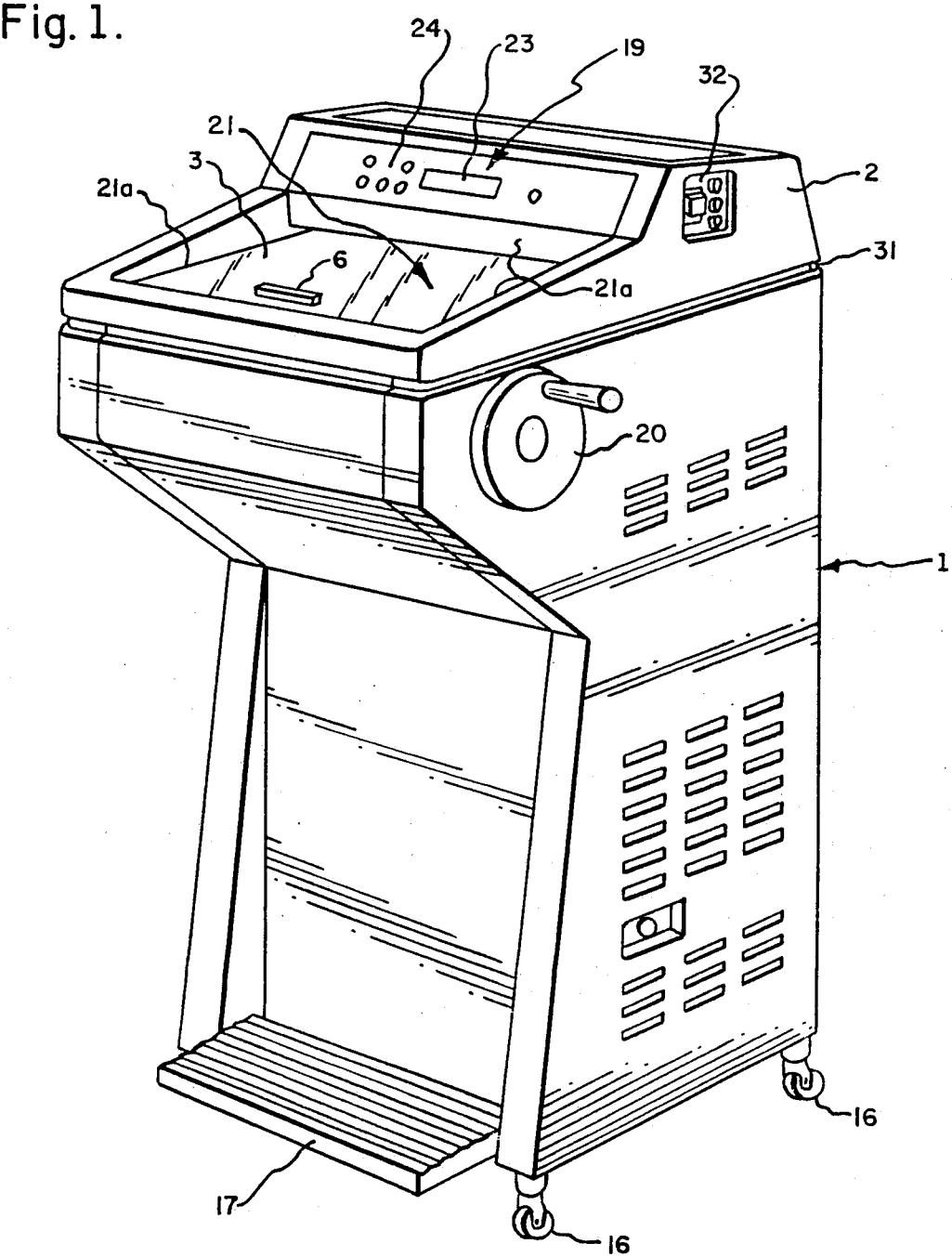
FIG. 1 is a perspective view of the device as a whole according to the invention.
Figure 2:
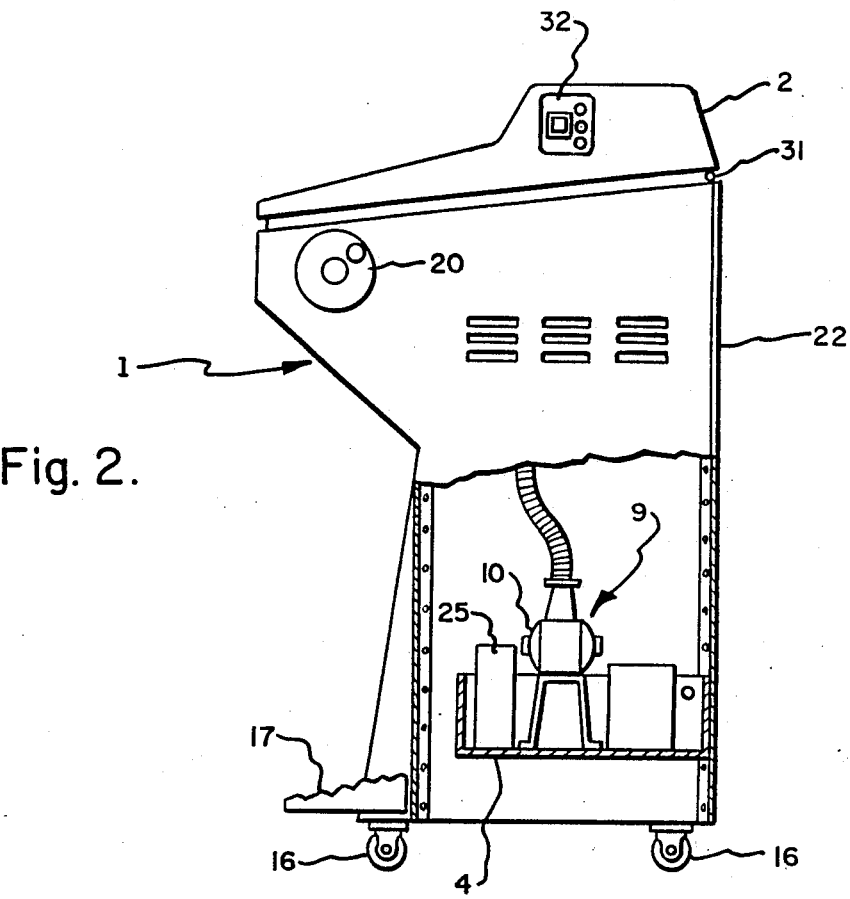
FIG. 2 is a right plan view, partly sectioned, of the device according to the invention.

FIGS. 1 and 2 show a foldaway frame (pivotable cover) 2, supported at the upper end of a desk-shaped instrument cabinet 1 and including a heatable glass pane 3. Frame 2 has a rear hinge 31 at the back of its rear portion, injection molded plastic part. The instrument cabinet 1 is self-contained without frame structure. As is shown in FIG. 2, the cabinet is merely riveted at folded-up rims of the lateral edges or welded at the edges. Sufficient stiffness of instrument cabinet 1 is accomplished by a trough-shaped aggregate(assembly) support 4 suspended in the lower part of the instrument cabinet. Before being suspended in the instrument cabinet, the aggregate support 4 is fitted with the refrigeration aggregate(assembly) 9 for the microtome, including compressor 10, heat regenerator 25 as well as various electric equipment for the device. If these aggregates(assemblies) need to be repaired, the aggregate support 4 with the aggregates mounted thereon can be taken off and removed from the instrument cabinet. As a result, the accessibility to the individual aggregates is improved.

In order for the device to be easily moved to and fixed in the individual working position guide rollers 16, which can be rotated 360° and arrested by means of stoppers, are secured to the underside of the desk-shaped instrument cabinet 1. In order for the user of the device to conveniently place his feet in front of the device during operation thereof footrest 17, which is tiltable about a horizontal axis, is provided at the front wall of the apparatus. When the device is transported, the footrest can be folded against the front wall of the device. For the event that only a passenger car or a light truck is available for transport of the device, plastic-coated slide rails 22 are provided on the back of the instrument cabinet 1 on which the device may rest during transport.

As is evident from FIGS. 4 to 6, heatable glass pane 3 is held by a pair of L-shaped guide rails 5 positioned below border 21a; protruding inwardly below opening 21 in cover 2, and being arranged in a configuration in which supporting surfaces of the rails face toward the top. The pane is provided with a handle 6 by means of which it can be slid from a first position below opening 21 in the direction of arrow A to a second position beneath the rear position of cover 2 in order to provide access to the microtome 7 disposed under the frame. In its first position, glass pane 3 can be gripped by handle 6 and, for cleaning purposes, moved upwardly out of its L-shaped guides 5.

When glass pane 3 is closed, the operation of microtome 7 can be observed through the pane. A daylight object illuminator 8 is provided above the cutter of the microtome to illuminate the microtome. As a result of glass pane 3 being heated by the daylight object illuminator, fogging of the pane disposed above the cooled microtome is inhibited. The major portion of the heating power is provided however in the—seen from the observer—front portion of glass pane 3 which is closer to the cooled microtome 7 and more remote from the heat dissipating daylight illumination means.

In order to facilitate exchange of the preparations, that is the specimens being cut, microtome 7 is provided with a rapid-exchange means which is not shown in the drawings and a likewise not shown rapid refrigerating station for three specimen supports. The entire microtome is arranged in a special steel vessel 15 including a discharge 30 to permit cleaning of the microtome in the installed state. Furthermore, handcrank 20 is provided at one sidewall of the instrument cabinet 1 for mechanically driving microtome 7.

As disclosed in FIG. 5, heating wires 11, which are disposed in conventional manner between upper glass layer 26 and lower glass layer 27 of glass pane 3, are connected to contacts 12. When glass pane 3 is in the closed position, said contacts 12 rest on counter contacts 13 fixedly provided in the device. Counter contacts 13 are connected by way of leads 14 with the non-depicted power supply for the pane heating means. FIG. 6 illustrates that the loops of heating wire 11 are closer to each other in the front portion of glass pane 3 than in the rearward portion to improve, as already explained, the heating power in the front portion.

Figure 3:
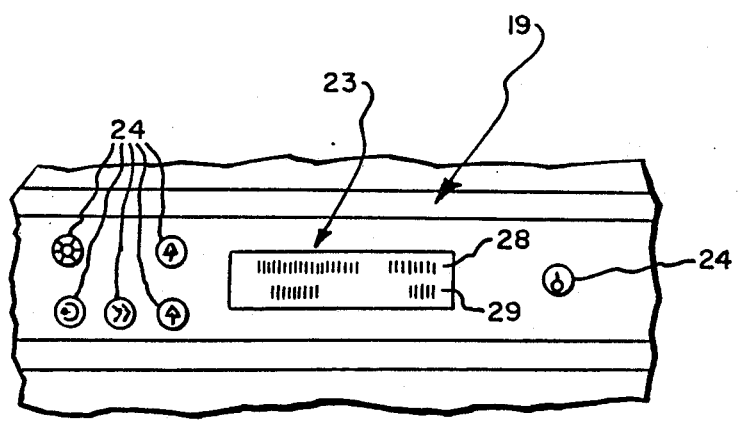
FIG. 3 an enlargement of a portion of the panel containing the alphanumeric display means.

FIG. 4 depicts a microprocessor 18 comprising two control boards arranged under foldaway frame 2 for controlling the functions of the device. The microprocessor can control all electric functions of the device including the microtome function. In order to facilitate the handling of the microtome and its auxiliary functions, the microprocessor operates in conversational communication with the user. This communication is enabled by a keyboard board which, together with liquid crystal display 23 and functions keys 24, forms keyboard 19 as designated in FIGS. 3 and 4.

By way of a menu-type function selection, the user can chose any desired operational mode. By means of a scroll control key, whose color stands out against the background, it is possible to go through the menu and select functions to be controlled. The desired values are changed by means of keys marked with arrows.

By using such combination of controls, it is possible to set, by means of only three keys, the distance from the object to be cut, the desired temperature, e.g. box temperature, the defrosting time and the reference time. A forth key permits switching the horizontal drive of the microtome between slow and rapid operation and vice versa. With the same key, an instant defrosting operation can be started in the "defrosting adjustment" menu.

The function keys can also be used to switch the cabinet illumination on and off and to lock the keyboard to prevent mistakes in operation.

All commands received through the keyboard are processed by the software contained in the processing board. Temperature control is digitally effected, i.e. the set desired value and the actual value of the box temperature delivered by a sensor in the form of a resistance value are compared in the microprocessor. As a result, corresponding signals are sent to the refrigeration unit.

A two-line liquid crystal display (LCD) is used as display means. The upper line 28 is to indicate to the user the current page of the menu. The lower line 29 indicates the status of the device. Normally, the upper display line indicates the current box temperature. When one of the "move keys" marked with the arrow symbols is pushed, the display switches to the "horizontal control" menu. In order to improve the operating safety, it is the above-mentioned mode which is selected first while the user goes through the menu by means of the scroll key. When the scroll key is held down, further menu pages will follow. If no change of the desired values is effected, the display switches back after a short time to the actual temperature.

The lower display line 29 can indicate whether the refrigeration unit is operating, whether defrosting is effected, the position of the horizontal drive and whether the cabinet illumination is switched on.

Switch keyboard 32, of FIGS. 1 and 2, illustrates a possible placement of general on/off switches for the major components of the device.

We claim:

1. An improved microtomy device wherein a microtome and a thermostatically controlled refrigeration means are accommodated in an instrument cabinet having a cover with a front portion an a rear portion, a hinge pivotably mounting said rear portion of said cover to said cabinet, border means in said front portion of said cover for defining an opening and a transparent pane closing the opening while permitting observation of the microtome in operation, the improvement comprising, a pair of guide rails protruding inwardly below opposing sides of said border means and extending beyond said border means under said rear portion, said pane being slidably carried by said pair of guide rails and movable from a first position below said border to a second rearward position, said second position of said pane permitting access to said microtome, and said first position permitting removal of said pane through the opening defined by said border.

2. The device according to claim 1, characterized in that the transparent pane is provided with a heating means, a power supply, and contact means for connecting said heating meant to said power supply when the shiftable pane is in first position.

3. The device according to claim 2, characterized in that the pane is provided with asymmetric heating wires to heat one portion of the pane is more than a second portion.

4. The device according to claim 1, wherein the pane is glass and a stainless steel vessel is mounted below said opening for supporting said microtome.

5. The device according to claim 1, comprising a handcrank mounted on a sidewall of said cabinet for driving the microtome.

6. The device according to claim 1 comprising a daylight illuminator arranged above a cutting edge of the microtome.

7. The device according to claim 1 wherein the instrument cabinet is of self contained construction and a substantially trough-shaped assembly support is suspended in the lower part of the cabinet.

8. The device according to claim 7, comprising refrigeration and electric assemblies mounted to the assembly support.

9. The device according to claim 1 comprising slide rails provided on the back of the instrument cabinet.

10. The device according to claim 1 comprising guide rollers provided on the underside of the instrument cabinet, which rollers can be rotated 360° and are arrestable, at least in part, by means of stoppers.

11. The device according to claim 1, wherein a microprocessor is provided for controlling the refrigeration means and the microtome.

12. The device of claim 11 wherein said microprocessor includes a keyboard comprising a liquid crystal display means and function keys.

13. The device according to claim 12, wherein the display means is an alphanumeric display means.

14. The device according to claim 13, wherein the display means is comprised in the cover, disposed above the inspection window and arranged at an obtuse angle from the horizontal.

15. The device according to claim 14, wherein the liquid crystal display comprises a menu line, from which functions can be selected by function keys, and a status line.

* * * * *